(12) United States Patent
Kim et al.

(10) Patent No.: US 12,702,685 B2
(45) Date of Patent: Aug. 11, 2026

(54) **ATTENUATED *SALMONELLA GALLINARUM* EXPRESSING FliC OR FliC-hIL2 AND USES THEREOF**

(71) Applicant: ODYSSEUS BIO CO., LTD., Jeollanam-do (KR)

(72) Inventors: Kwangsoo Kim, Gwangju (KR); Jong-eun Lee, Seoul (KR); Sol Choy, Seoul (KR)

(73) Assignee: ODYSSEUS BIO CO., LTD., Jeollanam-do (KR)

( * ) Notice: Subject to any disclaimer, the term of this patent is extended or adjusted under 35 U.S.C. 154(b) by 94 days.

(21) Appl. No.: 18/413,678

(22) Filed: Jan. 16, 2024

(65) Prior Publication Data

US 2024/0240140 A1 Jul. 18, 2024

(30) Foreign Application Priority Data

Jan. 16, 2023 (KR) ........................ 10-2023-0006245

(51) Int. Cl.

| | |
|---|---|
| ***A61K 35/74*** | (2015.01) |
| ***A61P 35/00*** | (2006.01) |
| ***C07K 14/195*** | (2006.01) |
| ***C07K 14/55*** | (2006.01) |
| ***C12N 15/74*** | (2006.01) |
| ***C12R 1/42*** | (2006.01) |

(52) U.S. Cl.

CPC .............. *A61K 35/74* (2013.01); *A61P 35/00* (2018.01); *C07K 14/195* (2013.01); *C07K 14/55* (2013.01); *C12N 15/74* (2013.01); *C07K 2319/00* (2013.01); *C12R 2001/42* (2021.05)

(58) Field of Classification Search

CPC ....... A61K 35/74; A61P 35/00; C07K 14/195; C07K 14/255; C12R 2001/42

See application file for complete search history.

(56) References Cited

PUBLICATIONS

Hajam et al. (2018). "Incorporation of membrane-anchored flagellin into Salmonella Gallinarum bacterial ghosts induces early immune responses and protection against fowl typhoid in young layer chickens. " Vet. Immunol. Immunopathol., 199:61-69. (Year: 2018).*

Hajam et al. (2017). "Bacterial flagellin—a potent immunostimulatory agent." Exp. Mol. Med. 49: e373. (Year: 2017).*

De Melo et al. (2014). "Anti-metastatic immunotherapy based on mucosal administration of flagellin and immunomodulatory P10." Immunol. Cell Biol., 93(1):86-98. (Year: 2014).*

Garaude and Blander. (2012). "Attacking tumor cells with a dual ligand for innate immune receptors." Oncogene, 3(4):361-362. ( Year: 2012).*

Brackett et al. (2016). "Toll-like receptor-5 agonist, entolimod, suppresses metastasis and induces immunity by stimulating an NK-dendritic-CD8+ T-cell axis." Proc. Natl. Acad. Sci. USA, 113(7):E874-E883. (Year: 2016).*

* cited by examiner

*Primary Examiner* — Daniel E Kolker
*Assistant Examiner* — Bailey M Morgan
(74) *Attorney, Agent, or Firm* — Sughrue Mion, PLLC

(57) ABSTRACT

Disclosed are attenuated *Salmonella gallinarum* expressing FliC (flagellin) or FliC-hIL2 (human IL2 fused to FliC) and use thereof, wherein the *Salmonella* strain exhibits excellent immune activation ability and anticancer efficacy and thus can be used as a cancer therapeutic agent, together with or independently from existing anticancer agents.

1 Claim, 11 Drawing Sheets

Specification includes a Sequence Listing.

【Fig 1】

| Gene | Mutated location | Results | Gene function |
|---|---|---|---|
| FlgI | Ser 109 | STOP | Basal body P ring |
| FlgK | Glu 125 | STOP | Hook-filament junction |
| FlhA | Glu 331 | STOP | Export apparatus; virulence hom olog |
| FlhB | From nucleotide 756 to 95 2 | Deleted | Suppress FliK mutation; virulen ce homolog |
| MotB | Nucleotide 687 | Framshift -1 | Motor rotation |
| FliK | Nucleotide 824, 825 | Framshift -2 | Hook length control |

【Fig 2】
*Salmonella Typhimurium*
(WT. ST)
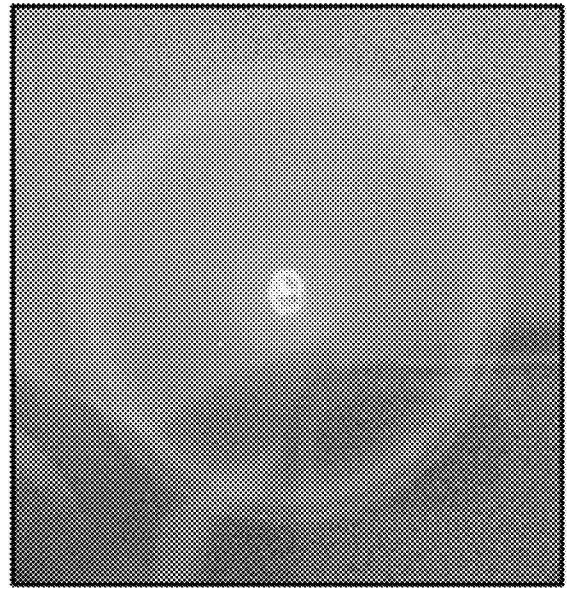
*Salmonella Gallinarum*
(WT. SG)
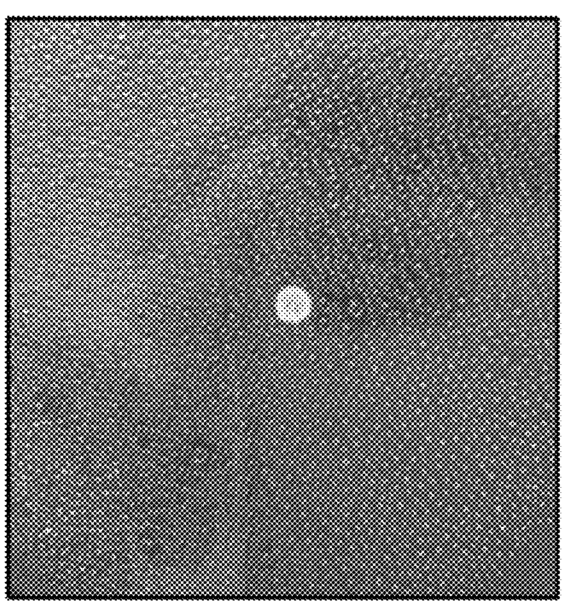

【Fig 3】
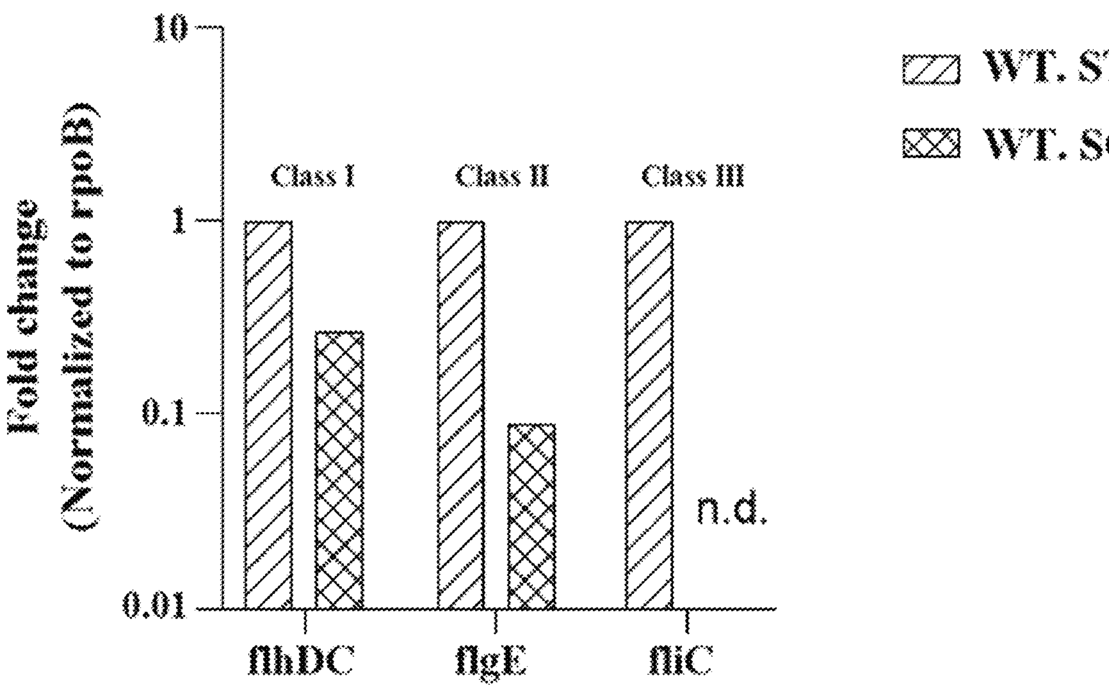

【Fig 4】
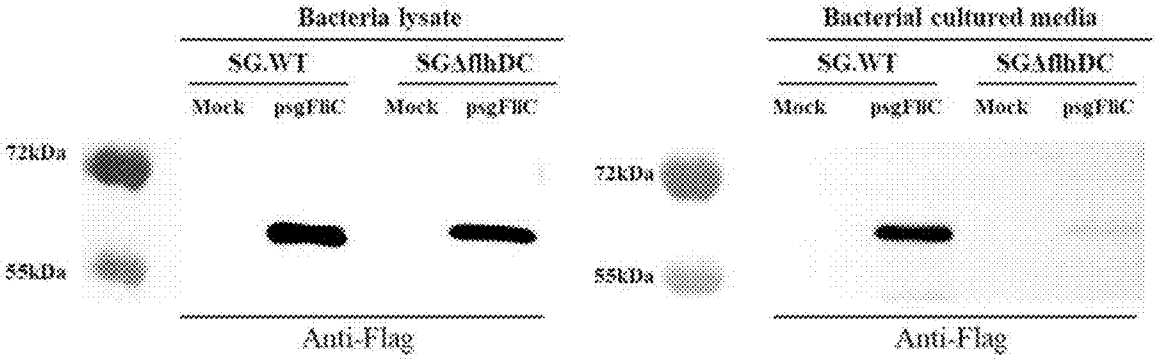
【Fig 5】
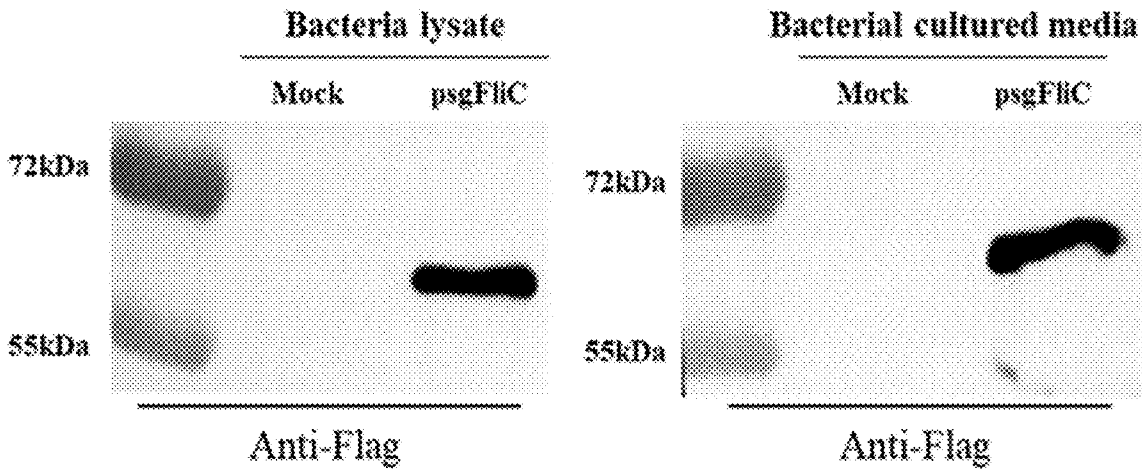

【Fig 6】
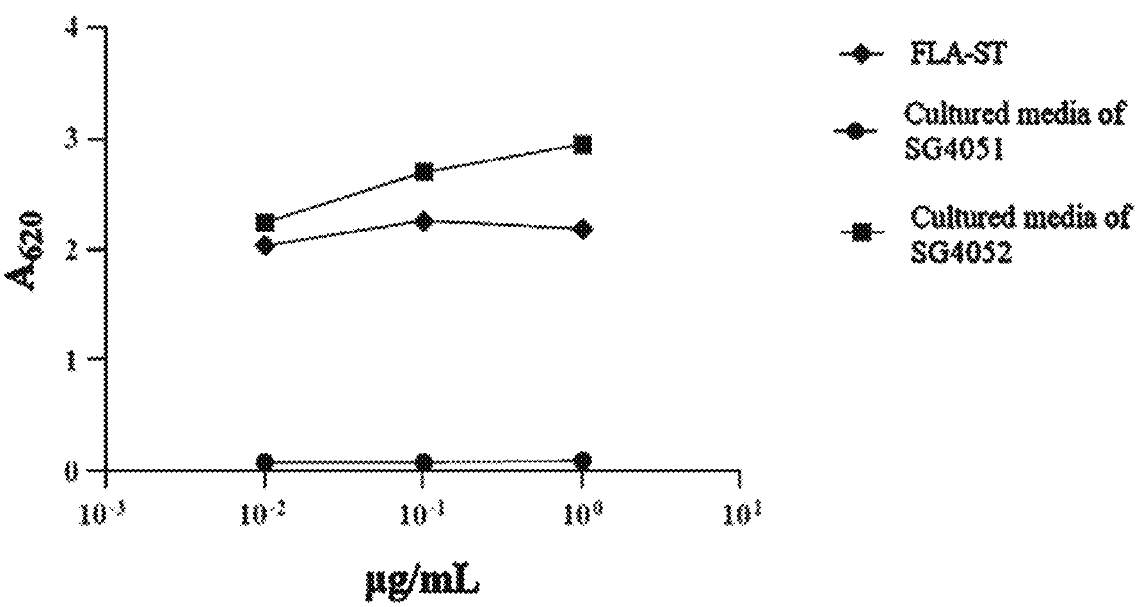
【Fig 7】
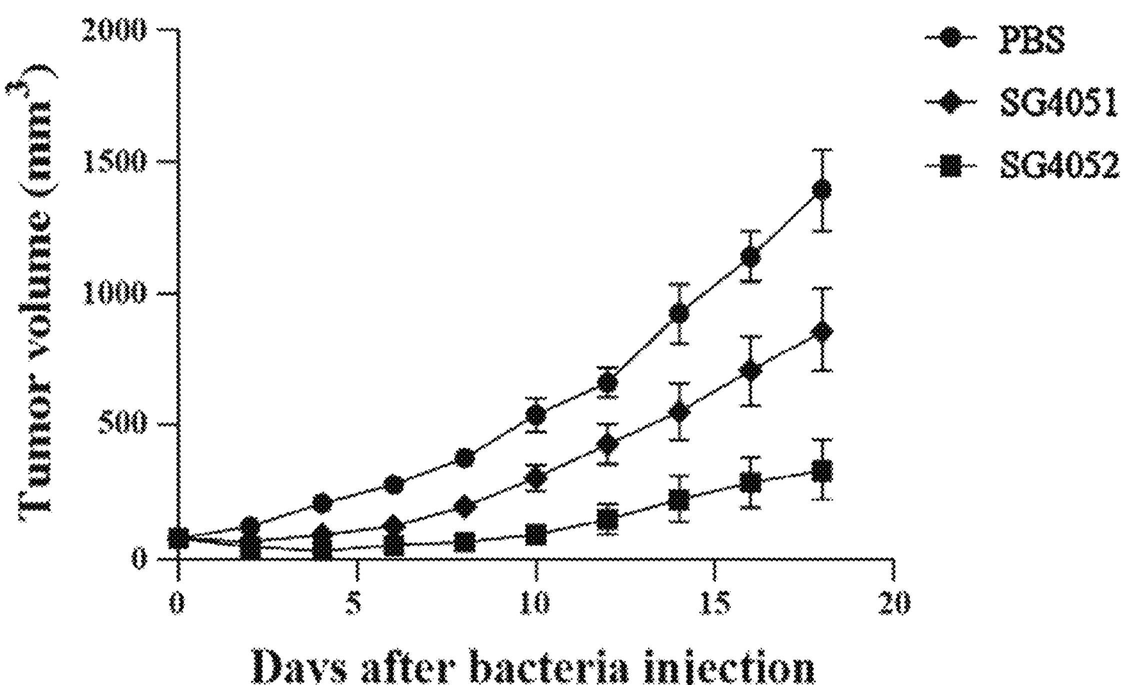

【Fig 8】
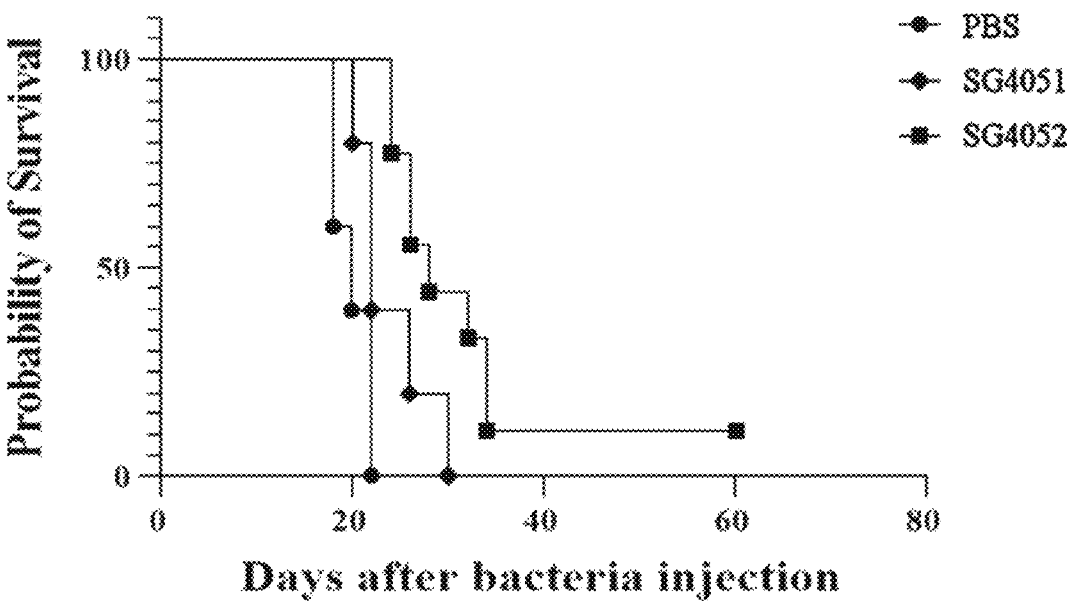
【Fig 9】
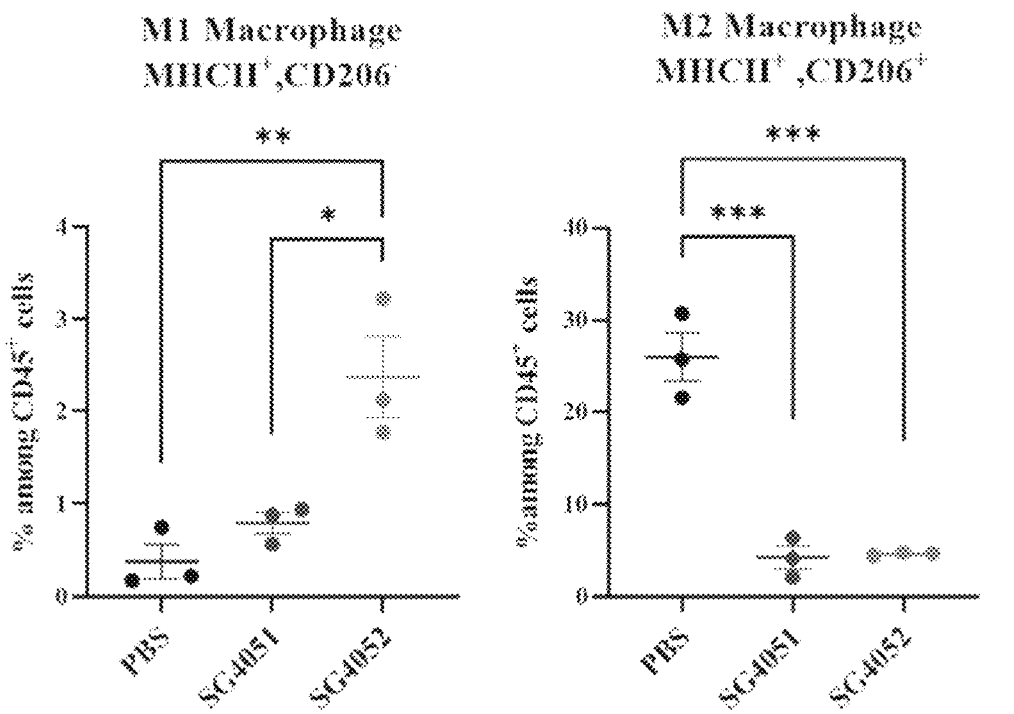

【Fig 10】
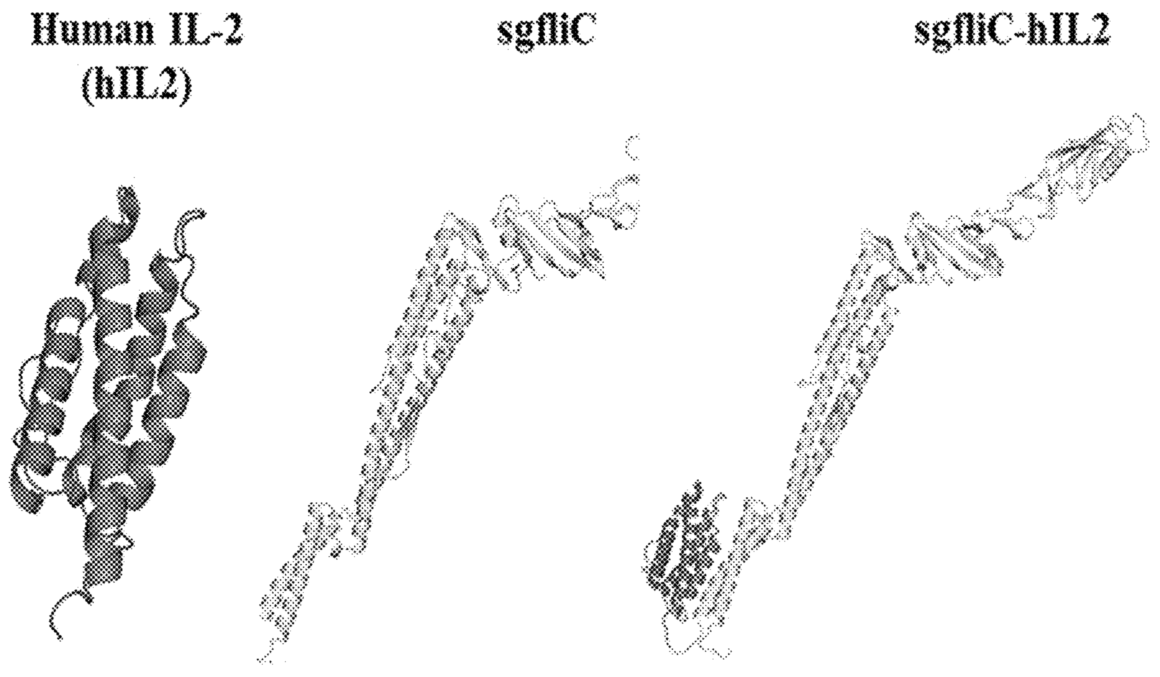
【Fig 11】
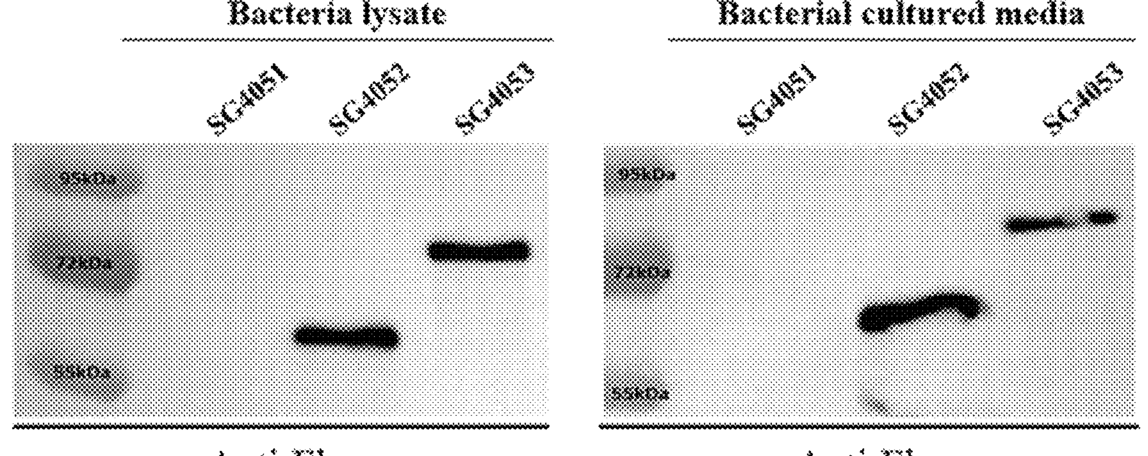

【Fig 12】
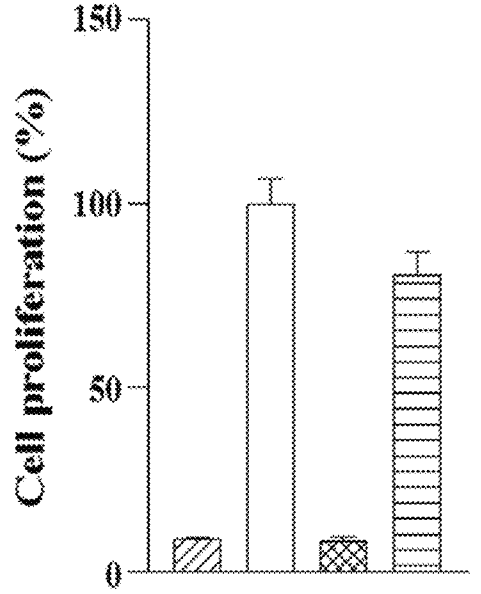
【Fig 13】
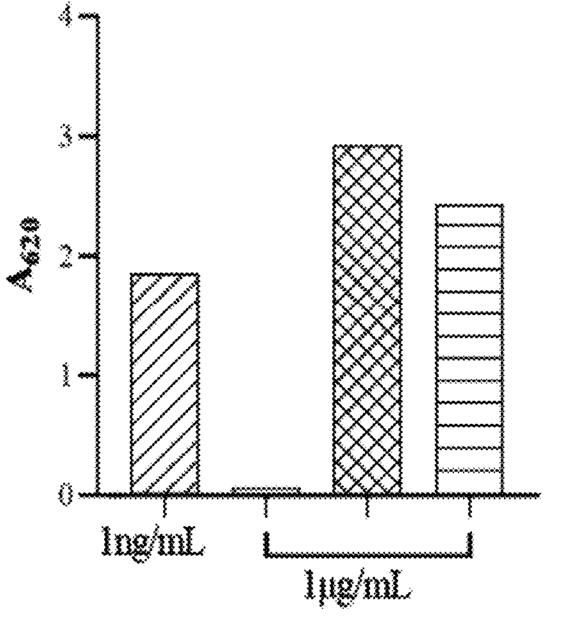

【Fig 14】
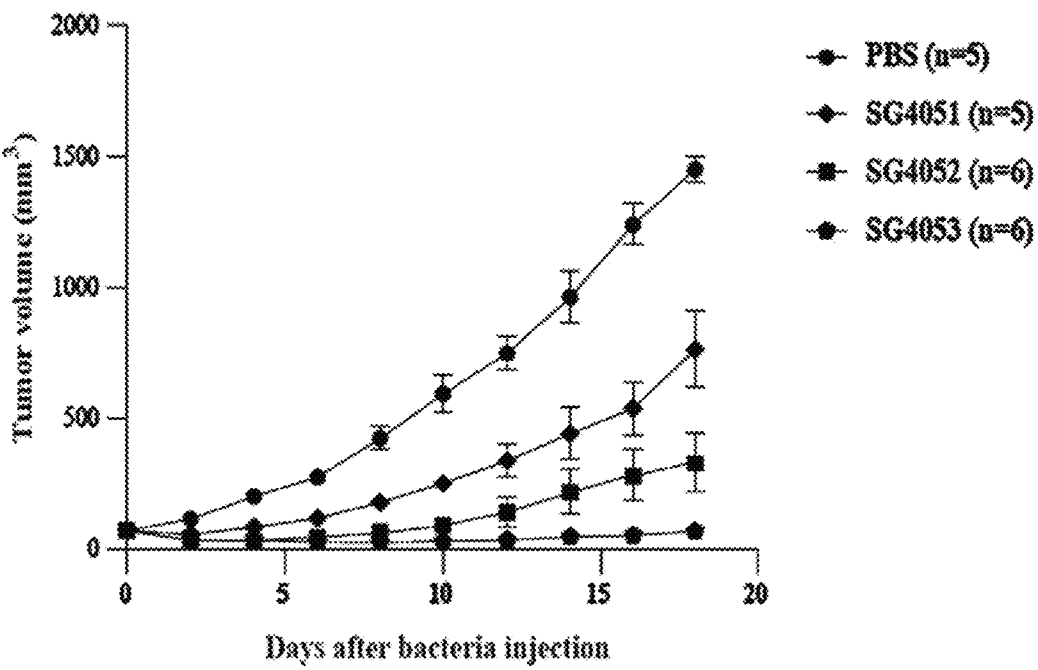
【Fig 15】
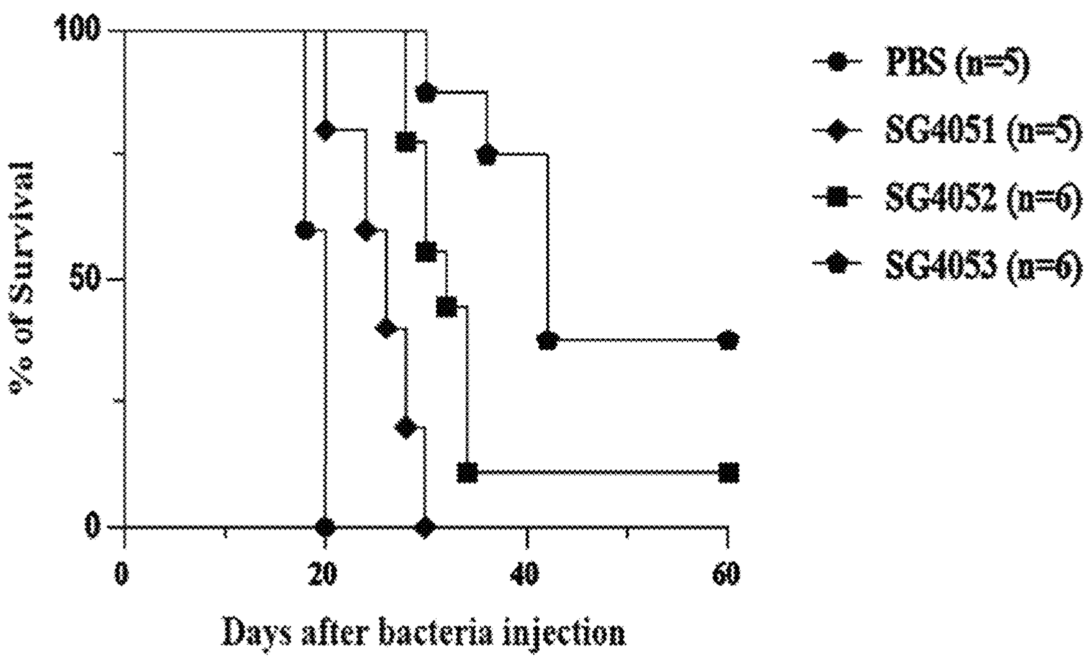

【Fig 16】
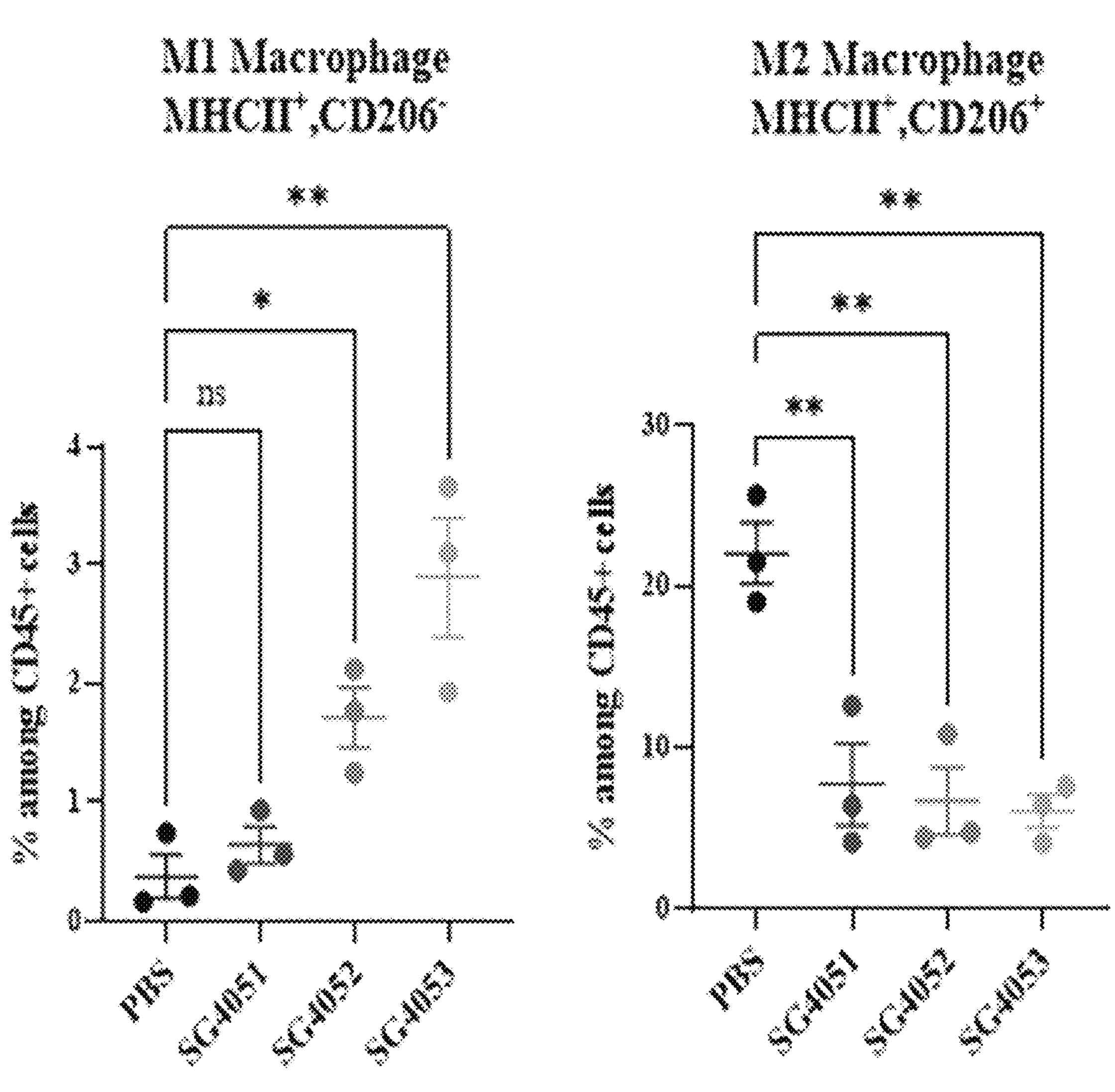

[Fig 17]
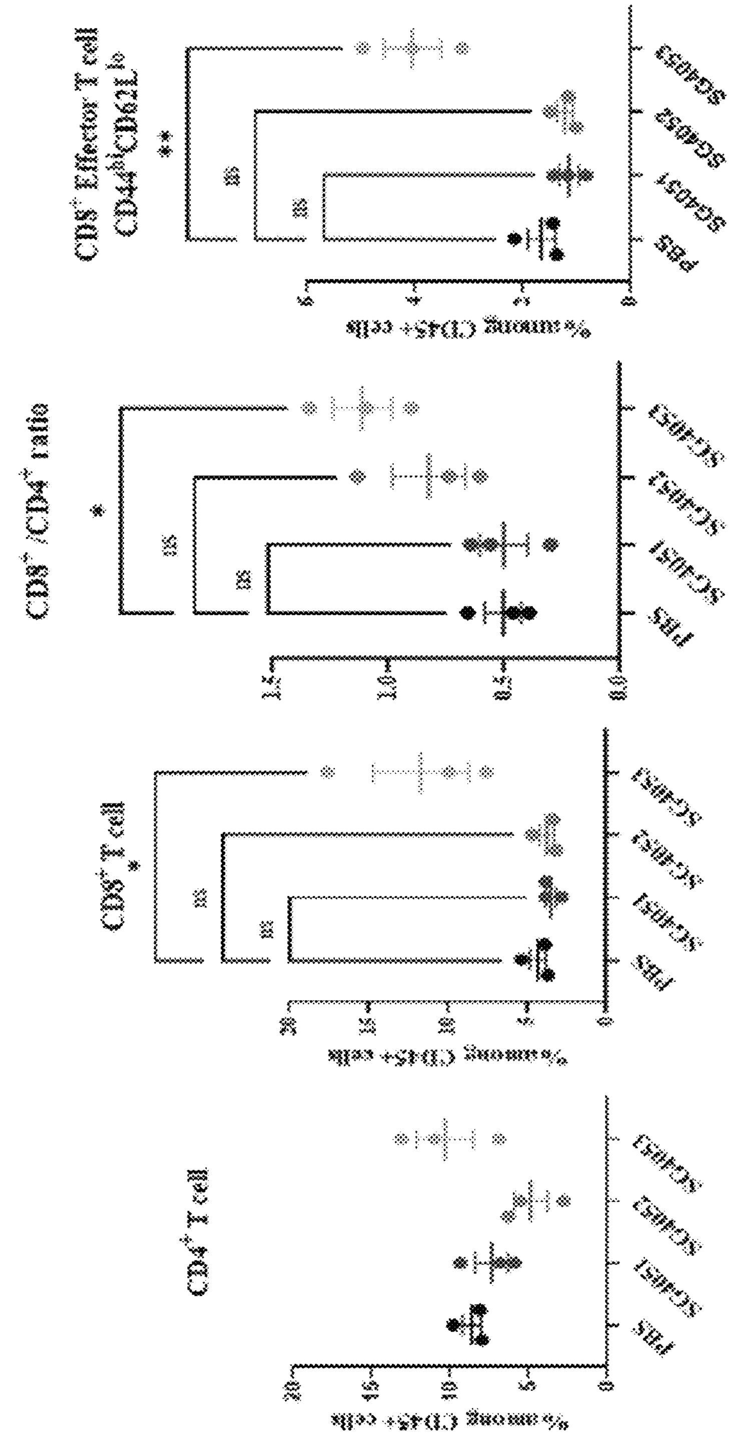

ATTENUATED *SALMONELLA GALLINARUM* EXPRESSING FliC OR FliC-hIL2 AND USES THEREOF

CROSS-REFERENCE TO RELATED APPLICATION

This application claims the benefit of Korean Patent Application No. 10-2023-0006245, filed Jan. 16, 2023, the entire disclosure of which is incorporated by reference.

INCORPORATION BY REFERENCE OF SEQUENCE LISTING

The content of the electronically submitted sequence listing, file name: Q295267_sequence listing as filed; size: 8,987 bytes; and date of creation: Jan. 12, 2024, filed herewith, is incorporated herein by reference in its entirety.

BACKGROUND OF THE INVENTION

1. Field of the Invention

The present disclosure relates to attenuated *Salmonella gallinarum* expressing FliC, a filament structural protein, or IL-2 protein fused with FliC, and use thereof and, more specifically, to a strain usable for immune activation ability and the treatment of tumor-related diseases and a vector or nucleic acid capable of transforming the strain.

2. Description of the Prior Art

In 2021, 161.1 people per 100,000 people died of cancer, accounting for 26.0% of all deaths. Therefore, cancer is considered to be the most common cause of death, and according to the National Cancer Information Center, the incidence rates have been increasing since 1999 when nationwide cancer incidence statistics began to be calculated.

The increases of the incidence rates of cancer-related diseases result from increases in environmental factors, such as increasing environmental pollutants including air pollution, and personal factors, such as intake of high fat diet due to the westernization of diet, drinking, and smoking. Therefore, the development of anti-cancer materials for early prevention and treatment of cancer is becoming more and more important. Additionally, refractory adenocarcinomas, for which there is no distinct therapy, have low incidence rates but high death rates, so the development of medicines therefor is urgently needed. However, many compound-based anticancer agents show non-specificity that the agents act on the whole body besides cancer cells, causing side effects.

Since bacterial infections were reported to exhibit anti-cancer effects, research on the development of anti-tumor bacterial strains has been rapidly increasing. Anti-tumor bacteria researched over the past 20 years are *Bifidobacterium, Clostridium, Lactococcus, Shigella, Vibrio, Listeria, Escherichia, Salmonella*, and the like. Albeit, mechanisms of cancer therapy using these strains have not yet been fully revealed, there is a need to develop new strains that have significantly higher tumor targeting ability and in vivo safety and can be effectively used for cancer treatment.

SUMMARY OF THE INVENTION

Accordingly, the present inventors produced an attenuated *Salmonella* strain designed to cause no problem due to the strain itself in a subject to be administered while having excellent immune activation ability by stimulating the TLR5 receptor through FliC expression, leading to outstanding anticancer activity.

Accordingly, an aspect of the present disclosure is to provide a polynucleotide that is introduced to a *Salmonella* strain (*Salmonella* sp.) to enhance the immune activation ability and anti-tumor efficacy of the *Salmonella* strain.

Another aspect of the present disclosure is to provide a *Salmonella* strain with excellent immune activation ability and anti-tumor efficacy.

Still another aspect of the present disclosure is to provide a pharmaceutical composition, containing a *Salmonella* strain with excellent immune activation ability and anti-tumor efficacy for treating, preventing, alleviating, or inhibiting cancer.

The present disclosure is directed to attenuated *Salmonella gallinarum* expressing FliC, a filament structural protein, or IL-2 protein fused with FliC, and use thereof, and the *Salmonella* strain according to the present disclosure has enhanced immune activation activity compared with existing *Salmonella* strains and thus has outstanding anticancer efficacy.

Hereinafter, the present disclosure will be described in more detail.

In accordance with an aspect of the present disclosure, there is provided a polynucleotide, which is introduced to a *Salmonella* strain to enhance immune activation ability and anti-tumor efficacy of the *Salmonella* strain, wherein the polynucleotide includes a polynucleotide encoding FliC, a filament structural protein.

As used herein, the term "polynucleotide" has a meaning collectively including a DNA or RNA molecule. A nucleotide, which is the basic structural unit of the polynucleotide, may include not only a natural nucleotide but also an analog with a modified sugar or base moiety.

In an embodiment of the present disclosure, the *Salmonella* strain may be an attenuated *Salmonella* strain.

As used herein, the term "attenuated" refers to being modified to lower the pathogenicity of a strain. Therefore, the attenuation of the *Salmonella* strain in the present disclosure can prevent the cytotoxicity and other side effects that may occur by the pathogenicity of the strain in animal cells. Attenuated strains can be achieved by various methods known in the art. For example, the attenuation may be achieved by the deletion or destruction of a virulence factor whereby a strain can survive in a host cell. The attenuation may be achieved by deletions of pab, proBC, nadA, pncB, pmi, rpsL, ompR, htrA, hemA, rfc, poxA, galU, aro, galE, cya, cyp, crp, cdt, pur, phoP, phoQ, ssa, guaA, guaB, clpP, clpX fliD, flgk, flgL, relA, spoA, and spoT genes, and the genes, encoded by *Salmonella* pathogenicity island (SPI), including ssaV, sseBCD, ssrAB, sopB, sseF, and sseG, but is not limited thereto.

In an embodiment of the present disclosure, the *Salmonella* strain may be *Salmonella gallinarum.*

As used herein, the term "*Salmonella gallinarum*" is a type of *Salmonella* strains that is morphologically gram-negative and mono-bacterial and lacks motility among *Salmonella* strains. The *Salmonella* strain that has been most frequently used for research on conventional targeted anti-cancer therapy using bacteria is *Salmonella typhimurium*, which is necessarily attenuated before use for research considering broad host range of *Salmonella typhimurium* infections. *Salmonella* spp. varies enough to be classified into approximately 2500 species according to the serological taxonomy, and some of the strains have been reported to possess host-specific pathogens. For example, it has been reported that *Salmonella typhi* and *Salmonella* paratyphi have pathogenic mechanisms that target a human as a host, and especially, *Salmonella typhimurium* causes diseases by infecting cattle, pigs, sheep, horses, and rodents as well as humans. Therefore, *Salmonella typhimurium* is still in danger of pathogenicity even when attenuated, and the administration of *Salmonella typhimurium* as anticancer agent or other drugs to subjects including humans is not appropriate. However, *Salmonella gallinarum* is known to show pathogenicity by specifically infecting only birds, and unlike *Salmonella typhimurium, Salmonella gallinarum* is significantly less likely to show pathogenicity in subjects including humans when attenuated additionally. Therefore, the attenuated *Salmonella typhimurium* strain of the present disclosure is safest for humans and can be effectively used for the diagnosis or treatment of tumors.

As used herein, the term "FliC" refers to a flagella filament structural protein found in bacteria. The FliC protein can stimulate toll-like receptor 5 to enhance the immune activity thereof. Wild-type *Salmonella gallinarum* cannot express and secrete FliC and thus cannot enhance the immune activity through the stimulation of toll-like receptor 5 in a subject. However, the *Salmonella gallinarum* strain according to the present disclosure expresses the FliC gene not expressed in the wild-type *Salmonella* strain, and thus can enhance immune activity in a subject to be administered. In addition, the *Salmonella gallinarum* strain according to the present disclosure can enhance the anticancer therapeutic efficacy through a synergistic action with the anticancer effect of the *Salmonella* strain itself (see Examples 3 to 4). In particular, the FliC protein can be secreted through the type III secretion system within the attenuated *Salmonella gallinarum* transformed according to the present disclosure.

In an embodiment of the present disclosure, the polynucleotide may further include a polynucleotide encoding interleukin-2 (IL-2) fused with FliC.

In an embodiment, the polynucleotide may further include a polynucleotide encoding at least one selected from the group consisting of interleukin-1 beta (IL-1β), interleukin-10 (IL-10), interleukin-15 (IL-15), interleukin-7 (IL-7), interleukin-21 (IL-21), granulocyte-macrophage colony-stimulating factor (GM-CSF), tumor necrosis factor-alpha (TNF-α), and interferon-γ (IFNγ).

In an embodiment of the present disclosure, the polynucleotide may encode FliC, which is a filament structural protein, fused with interleukin-2 (IL-2).

In an embodiment of the present disclosure, the polynucleotide may encode FliC, which is a filament structural protein, fused with at least one selected from the group consisting of interleukin-1 beta (IL-1β), interleukin-10 (IL-10), interleukin-15 (IL-15), interleukin-7 (IL-7), interleukin-21 (IL-21), granulocyte-macrophage colony-stimulating factor (GM-CSF), tumor necrosis factor-alpha (TNF-α), and interferon-γ (IFNγ).

Therefore, the *Salmonella* strain according to the present disclosure can express both FliC and IL-2, especially, IL-2 protein fused with FliC. The *Salmonella* strain of the present disclosure expressing the IL-2 protein fused with FliC has immune activity stimulating ability by stimulating the TLR5 receptor in a subject through FliC expression, and has excellent immune cell activation ability by selectively increasing $CD8^+$ T cells ($CD3^+$, $CD8^+$) in tumors through IL-2 (see Example 7). As described above, FliC can be secreted through the type III secretion system in a *Salmonella* strain, and thus the IL-2 protein fused with FliC can also be secreted together with FliC outside the *Salmonella* strain through the type III secretion system. Therefore, the *Salmonella* strain according to the present disclosure can secrete the FliC and IL-2 proteins through the type III secretion system rather than the other type secretion system in gram-negative bacteria. Specifically, the FlaB protein is generally secreted through the type II secretion system, and thus often uses the signal sequence held by the PelB protein by fusion thereto in order to deliver a protein, present in a periplasmic space between the cell wall and the cell membrane, to the outside of the cell wall. However, in the present disclosure, FliC and IL-2 fused therewith through the type III secretion system as described above need not be delivered outside the *Salmonella* strain through the use of a separate sequence of the PelB protein.

As used herein, the term "expression" includes any step involved in the production of a polypeptide, such as transcription, post-transcriptional modification, translation, post-translation modification, and secretion, but is not limited thereto. The *Salmonella* strain according to the present disclosure can express FliC or both FliC and IL-2, and secrete and produce FliC and/or IL-2 as well as express FliC or FliC and IL-2, and especially, express IL-2 protein fused with FliC.

In an embodiment of the present disclosure, the polynucleotide encoding FliC may include the sequence of SEQ ID NO: 1.

In an embodiment of the present disclosure, the polynucleotide encoding interleukin-2 fused with FliC may include the sequence of SEQ ID NO: 3.

As used herein, the term "substantial identity" means that, when each nucleotide sequence and any other nucleotide sequence are aligned to correspond to each other as much as possible and analyzed, the any other nucleotide sequence may include a polynucleotide having a sequence homology of 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% to each nucleotide sequence and, a sequence homology of for example, 90%.

In accordance with another aspect of the present disclosure, there is provided a *Salmonella* strain, to which a vector containing a polynucleotide encoding FliC, a filament structural protein, is introduced.

In the present disclosure, the *Salmonella* strain may be an attenuated *Salmonella* strain transformed through a vector.

As used herein, the term "transformation" refers to a process of introducing a vector, containing a polynucleotide encoding a target protein, to a host cell so that the protein encoded by the polynucleotide can be expressed in the host cell. The transformed polynucleotide may be inserted into the chromosome of a host cell and located thereon or located outside of the chromosome as long as the transformed polynucleotide can be expressed in the host cell. Additionally, the polynucleotide includes DNA or RNA encoding the target protein. The polynucleotide may be introduced in any form as long as the polynucleotide can be introduced to the host cell and expressed therein. For example, the polynucleotide may be introduced to the host cell in the form of an expression cassette, which is a gene construct including all elements required for its autonomous expression, or in the form of a vector including the expression cassette.

As used herein, the term "vector" refers to a means for expressing a target gene in a host cell. Examples of the vector may include plasmid vectors, cosmid vectors, and viral vectors, such as bacteriophage vectors, adenovirus vectors, retrovirus vectors, and adeno-associated viral vectors.

Vectors that can be used as a recombinant vector may include any vector used in the art without limitation. Specifically, the vector may be constructed using plasmids, such as pAWP89, pBAD, pCES208, pSC101, pGV1106, pACYC177, ColE1, pKT230, pME290, pBR322, pUC8/9, pUC6, pBD9, pHC79, pIJ61, pLAFR1, pHV14, pGEX series, pET series, and pUC19, phages, such as λgt4λB, λ-Charon, λΔz1, and M13, or virus vectors, such as SV40, but is not limited thereto.

In the present disclosure, the delivery (introduction) of the recombinant vector into a microorganism (host cell) may employ a delivery method widely known in the art. For example, the delivery method may employ a $CaCl_2$) method, an electroporation method, or the like when the host cell is a prokaryotic cell, and may employ a microinjection method, a calcium phosphate precipitation method, an electroporation method, a liposome-mediated transfection method, a gene bombardment method, or the like, but is not limited thereto.

The transformed host cells may be easily selected by a method widely known in the art, using a phenotype expressed by a selective label. For example, if the selective label is a specific antibiotic resistant gene, transformants can be easily selected by culturing transformants in media containing antibiotics.

In an embodiment of the present disclosure, the *Salmonella* strain may be *Salmonella gallinarum.*

The present inventors named the transformed strain as attenuated *Salmonella gallinarum* carrying psgFliC (SG4052) and deposited the strain on 4 Jan. 2023 with the Korean collection for type cultures (KCTC) at the Korea Research Institute of Bioscience and Biotechnology and assigned accession number KACC 15269BP.

In an embodiment of the present disclosure, the *Salmonella* strain may be a strain deposited under accession number KACC 15269BP.

In one embodiment of the present disclosure, the *Salmonella* strain may be deleted in any one gene selected from the group consisting of a gene encoding guanosine tetraphosphate (ppGpp) synthase, ssrA/B as a transcriptional active factor of *Salmonella* pathogenicity island 2, and a Gifsy-2 prophage gene.

As used herein, the term "ppGpp" refers to guanosine tetraphosphate and may be used interchangeably with guanosine 5'-diphosphate 3'-diphosphate or guanosine 3',5'-bispyrophosphate. The ppGpp, which is an intracellular signaling substance, induces the expression of genes encoded by *Salmonella* pathogenicity island (SPI) among the genes responsible for the virulence of *Salmonella gallinarum* strains. In the present disclosure, the genes encoding guanosine tetraphosphate (ppGpp) synthase may mean relA and spoT genes.

The deletions of both the relA and spot genes may be achieved by the modifications of the relA and spoT genes that cause the impairment to the transcription or translation of the genes or the activity of the gene products. Such genetic modifications may include not only the inactivation of a ppGpp synthetase coding sequence (CDS) but also the inactivation of a promoter thereof.

The specific inactivation of only a target gene on the genome of a *Salmonella gallinarum* strain may be achieved by the mutation through substitution, insertion, deletion, or a combination thereof on the entire region or at least one partial region of the coding gene. For example, the deletion of a gene or the insertion of a heterogeneous sequence into a gene may result in gene truncation, nonsense mutation, frameshift mutation, missense mutation, or the like. Such the specific inactivation of genes may be performed using a method that is usually used in the art. Meanwhile, the deletion of a gene may be performed by various mutagenesis methods that are known in the art. For example, the deletions of the relA and spot genes may be achieved by PCR mutagenesis and cassette mutagenesis.

As used herein, the term "type III secretion system (T3SS)" is regulated by ssrA and ssrB genes that are sequentially arranged on the genome. The transcriptional regulator ssrB is phosphorylated by the membrane protein ssrA to have activity. Therefore, the loss of functions through the removal of ssrA and/or ssrB on the genome of *Salmonella gallinarum* may result in the inactivation of the operon and all genes included in the *Salmonella* pathogenicity island 2 (SPI2). After infection into a host, *Salmonella* distributes the type III secretion system (T3SS) encoded by SPI2 to modify functions of the host cell and reproduce within the host cell.

In the present disclosure, Gifsy-1 and -2 mean viruses (bacteriophages) targeting bacteria. The present inventors verified according to the genomic test results of wild-type *Salmonella gallinarum* that the entire gene sequence encoding Gifsy-2 prophage is included in the genome. The deletion of the gene inserted into the *Salmonella* genome can lower the pathogenicity of *Salmonella.*

In an embodiment of the present disclosure, the *Salmonella* strain may have a deletion of the glmS gene.

The glmS gene-deleted *Salmonella gallinarum* strain may be lysed in an animal due to the lack of D-glucosamine (GlcN) or N-acetyl-D-glucosamine (GlcNAc), which is a component for peptidoglycan synthesis, so that the glmS gene instead of antibiotic-resistant genes can be used as a selective determinant for the *Salmonella gallinarum* strain.

In an embodiment, the *Salmonella* strain may be deleted in relA, spoT, ssrAB, Gifsy-2 prophage, and glmS genes.

In an embodiment of the present disclosure, the vector may further include a polynucleotide encoding interleukin-2 (IL-2).

In an embodiment of the present disclosure, the vector may further include a polynucleotide encoding FliC, a filament structural protein, fused with interleukin-2 (IL-2).

The present inventors named a strain transformed by the introduction of a polynucleotide encoding FliC, a filament structural protein, fused with interleukin-2 (IL-2) as attenuated *Salmonella gallinarum* carrying psgFliC-hIL2 (SG4053) strain and deposited on 4 Jan. 2023 with the Korean collection for type cultures (KCTC) at the Korea Research Institute of Bioscience and Biotechnology and assigned accession number KACC 15270BP.

In an embodiment of the present disclosure, the *Salmonella* strain may be a strain deposited under accession number KACC 15270BP.

In an embodiment of the present disclosure, the vector may further include a polynucleotide encoding at least one selected from the group consisting of interleukin-1 beta (IL-1β), interleukin-10 (IL-10), interleukin-15 (IL-15), interleukin-7 (IL-7), interleukin-21 (IL-21), granulocyte-macrophage colony-stimulating factor (GM-CSF), tumor necrosis factor-alpha (TNF-α), and interferon-γ (IFNγ).

In accordance with still another aspect of the present disclosure, there is provided a pharmaceutical composition for preventing, alleviating, or inhibiting cancer, the pharmaceutical composition containing, as an active ingredient, a *Salmonella* strain to which a vector containing protein, is introduced.

As used herein, the term "containing as an active ingredient" means that the pharmaceutical composition according to the present disclosure contains an attenuated *Salmonella* strain at an amount sufficient to achieve alleviating, inhibiting, preventing, or therapeutic activity against cancer or tumor-related diseases.

In an embodiment of the present disclosure, the *Salmonella* strain may have a vector introduced thereto, the vector containing a polynucleotide encoding FliC, a filament structural protein, and a polynucleotide encoding interleukin-2 (IL-2).

In an embodiment of the present disclosure, the *Salmonella* strain may have a vector introduced thereto, the vector containing a polynucleotide encoding FliC, a filament structural protein, fused with interleukin-2 (IL-2).

In an embodiment, the *Salmonella* strain may have a vector introduced thereto, the vector containing a polynucleotide encoding FliC, a filament structural protein, fused with at least one selected from the group consisting of interleukin-1 beta (IL-1β), interleukin-10 (IL-10), interleukin-15 (IL-15), interleukin-7 (IL-7), interleukin-21 (IL-21), granulocyte-macrophage colony-stimulating factor (GM-CSF), tumor necrosis factor-alpha (TNF-α), and interferon-γ (IFNγ).

In the present disclosure, the pharmaceutical composition may contain a pharmaceutically acceptable carrier, and examples thereof may include lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methyl hydroxy benzoate, propyl hydroxy benzoate, talc, magnesium stearate, mineral oils, and the like, but are not limited thereto.

In the present disclosure, the pharmaceutical composition may further contain a lubricant, a wetting agent, a sweetening agent, a flavoring agent, an emulsifier, a suspending agent, a preservative, and the like.

In the present disclosure, the pharmaceutical composition may be administered orally or parenterally, for example, by intravenous injection, subcutaneous injection, intramuscular injection, intraperitoneal injection, topical administration, intranasal administration, intrapulmonary administration, intrarectal administration, intrathecal administration, ocular administration, dermal administration, transdermal administration, or the like, but is not limited thereto.

In the present disclosure, the dose of the pharmaceutical composition may be variously determined depending on factors, such as formulation method, administration manner, patient's age, body weight, and sex, pathological condition, diet, administration time, administration route, excretion rate, and response sensitivity, and the dose may be determined and prescribed as an amount effective for desired treatment or prevention. For example, the dose per day of the pharmaceutical composition of the present disclosure may be $1\times10^5$-$1\times10^9$ bacteria/kg. Bacterial numbers are counted using hemocytometer.

In the present disclosure, the pharmaceutical composition may be formulated by using a pharmaceutically acceptable carrier and/or excipient according to a method that can be easily performed by a person skilled in the art to which the present disclosure pertains, and thus the pharmaceutical composition may be provided as a unit dosage form or may be packed in a multi-dose container. Particularly, the pharmaceutical composition may be in the form of a solution in an oily or aqueous medium, a suspension, an emulsion, an extract, a pulvis, a suppository, a powder, granules, a tablet, or a capsule, and may further contain a dispersant or a stabilizer, but is not limited thereto.

The dose of the pharmaceutical composition of the present disclosure may vary depending on patient's age, body weight, and sex, the form of administration, health condition, and disease severity, and may be divisionally administered once or several times at predetermined time intervals according to the determination of a doctor or pharmacist. For example, the dose per day may be $1\times10^5$-$1\times10^9$ bacteria/ml on the basis of the number of bacteria counted, but this is an example of an average case, and the dose may be high or low depending on individual differences.

As used herein, the term "treatment of cancer" refers to any action that suppresses cancer, and specifically, may mean a cycle control action of cancer cells or an apoptosis induction action of cancer cells, but is not limited thereto.

In an embodiment of the present disclosure, the cancer may be at least one selected from the group consisting of breast cancer, lung cancer, stomach cancer, liver cancer, blood cancer, bone cancer, pancreatic cancer, skin cancer, head or neck cancer, skin or eye melanoma, uterine sarcoma, ovarian cancer, rectal cancer, anal cancer, colorectal cancer, fallopian tubal cancer, endometrial cancer, cervical cancer, small intestine cancer, endocrine cancer, thyroid cancer, parathyroid cancer, kidney cancer, soft tissue tumor, urethral cancer, prostate cancer, bronchial cancer, glioblastoma, and bone marrow cancer.

The present disclosure is directed to a *Salmonella* strain expressing FliC or FliC-hIL2 and use thereof, and the *Salmonella* strain according to the present disclosure exhibits excellent immune activation ability and outstanding immune activation ability and thus can be used as a cancer therapeutic agent together with or independent from an existing strain.

BRIEF DESCRIPTION OF THE DRAWINGS

The above and other aspects, features, and advantages of the present disclosure will be more apparent from the following detailed description taken in conjunction with the accompanying drawings.

FIG. 1 shows the results of identifying the mutation of flagellin biosynthesis-associated genes of wild-type *Salmonella gallinarum* according to an example of the present disclosure.

FIG. 2 provides images showing the results of identifying the motility of wild-type *Salmonella typhimurium* (WT. ST) and wild-type *Salmonella gallinarum* through bacterial motility assay according to an example of the present disclosure.

FIG. 3 provides a graph showing the results of identifying, through QPCR, the mRNA levels of flhD/C, flgE, and FliC linked to the Flagella operon in *Salmonella typhimurium* and *Salmonella gallinarum* according to an example of the present disclosure.

FIG. 4 shows the results of identifying the secretion ability of *Salmonella gallinarum*-derived FliC through the type III secretion system according to an example of the present disclosure.

FIG. 5 shows the results of identifying intracellular and extracellular secretion ability of sgFliC according to an example of the present disclosure.

FIG. 6 provides a graph showing the results of identifying toll-like receptor 5 (TLR5)-stimulating ability of sgFliC according to an example of the present disclosure.

FIG. 7 provides a graph showing the results of identifying the tumor size reduction by the administration of the *Salmonella gallinarum* SG4052 strain according to an example of the present disclosure.

FIG. 8 provides a graph showing the results of identifying the survival rate increase by the administration of the *Salmonella gallinarum* SG4052 strain according to an example of the present disclosure.

FIG. 9 provides graphs showing the results of identifying the distributions of M1 and M2 macrophages in the tumor by the administration of the *Salmonella gallinarum* SG4052 strain according to an example of the present disclosure.

FIG. 10 shows the results of predicting the structures of human IL-2, sgFliC, and sgFliC-hIL2 according to an example of the present disclosure.

FIG. 11 shows the results of detecting the protein expression of sgFliC and sgFliC-hIL2.

FIG. 12 provides a graph showing the results of evaluating the IL-2 function of sgFliC and sgFliC-hIL2 according to an example of the present disclosure.

FIG. 13 provides a graph showing the results of evaluating TLR5 activation ability of sgFliC and sgFliC-hIL2 according to an example of the present disclosure.

FIG. 14 provides a graph showing the results of observing the tumor size change by the administration of the *Salmonella gallinarum* SG4053 strain according to an example of the present disclosure.

FIG. 15 provides a graph showing the results of observing the survival rate change by the administration of the *Salmonella gallinarum* SG4053 strain according to an example of the present disclosure.

FIG. 16 provides graphs showing the results of identifying the distributions of macrophages in the tumor by the administration of the *Salmonella gallinarum* SG4053 strain according to an example of the present disclosure.

FIG. 17 provides graphs showing the results of identifying the distributions of T cells in the tumor by the administration of the *Salmonella gallinarum* SG4053 strain according to an example of the present disclosure.

DETAILED DESCRIPTION OF THE EXEMPLARY EMBODIMENTS

Hereinafter, the present disclosure will be described in more detail by the following exemplary embodiments. However, these exemplary embodiments are used only for illustration, and the scope of the present disclosure is not limited by these exemplary embodiments.

Example 1: Analysis of Motility and FliC Expression of *Salmonella gallinarum*

The mutations in genes associated with flagellin biosynthesis were confirmed through whole genome sequencing of wild-type *Salmonella gallinarum*, and the results are shown in FIG. 1.

Subsequently, the motility of wild-type *Salmonella gallinarum* and wild-type *Salmonella typhimurium* was verified through bacterial motility assay, and the results are shown in FIG. 2. As shown in FIG. 2, wild-type *Salmonella gallinarum*, unlike wild-type *Salmonella typhimurium*, was identified to have no motility.

The mRNA levels of flhD/C (Class I), flgE (Class II), and FliC (Class III), representative genes involved in flagellin biosynthesis, were verified through QPCR, and the results are shown in FIG. 3. Particularly, flhD/C, flgE, and FliC of *Salmonella typhimurium* were used as controls for this experiment. As can be seen in FIG. 3, the expression levels of flhD/C and flgE genes in wild-type *Salmonella gallinarum* were reduced by approximately 30% and 50% compared with the controls, respectively. The flic expression in the attenuated *Salmonella gallinarum* was not detected. These results indicate that most of the genes involved in the flagellin biosynthesis in *Salmonella gallinarum* were not activated or lowly expressed. Taken together, the lack of expression of flagellin in *Salmonella gallinarum* is inferred to result from a lack of necessary sigma factors.

Example 2: Identification of Type III Secretion-Dependent Extracellular Secretion Ability of *Salmonella gallinarum*-Derived FliC It is known that FliC from Enteropathogenic *Escherichia coli* (EPEC) is extracellularly secreted through the Type III secretion system (T3SS) to stimulate TLR5 signal but is not involved in motility. In addition, FliC, known as the filament structural protein of *Salmonella typhimurium*, is known to be extracellularly secreted.

It was identified that sgFliC was not produced in wild-type *Salmonella gallinarum* (see FIG. 3). Therefore, an sgFliC overexpression construct (psgFliC) and a control construct (Mock) each were transformed into wild-type *Salmonella gallinarum* (SG. WT) and FlhD/C-mutated *Salmonella gallinarum* (SGΔflhD/C), and it was investigated whether sgFliC was produced and extracellularly secreted in each type of bacteria, and the results are shown in FIG. 4.

As can be shown in FIG. 4, sgFliC from wild-type *Salmonella gallinarum* was extracellularly detected (in bacterial cultured media), but a very low level of sgFliC was detected in the *Salmonella gallinarum* strain lacking flhD/C, a master gene in the flagellin biosynthesis. These results indicate that flagellin is not produced but T3SS is functionally maintained in wild-type *Salmonella gallinarum.*

Example 3: Evaluation of Anti-Tumor Efficacy of sgFliC-Secreted Attenuated *Salmonella gallinarum*

To evaluate the anti-tumor efficacy of sgFliC, psgFliC having the sequences shown in Table 1 below was transformed into the attenuated *Salmonella gallinarum* strain SG4048 (ΔrelA, Δspot, ΔssrAB, ΔGifsy-2 prophage, and ΔglmS) to produce a sgFliC-secreted attenuated *Salmonella gallinarum* strain (SG4052). In addition, the SG4052 strain was deposited on 4 Jan. 2023 with the Korean collection for type cultures (KCTC) at Korea Research Institute of Bioscience and Biotechnology and assigned accession number KACC 15269BP. In addition, Mock was transformed into SG4048 to produce a bacterium that could be used as a control for subsequent experiments (SG4051). The sgFliC was strongly detected in the cytoplasm and outside the cells in SG4052 but not in SG4051 (see FIG. 5).

TABLE 1

| SEQ ID NO | Name | Sequence (5' -> 3') | Note |
|---|---|---|---|
| 1 | fliC | ATGGCACAAGTCATTAATACAAACAGCCTGTCGCT GTTGACCCAGAATAACCTGAACAAATCTCAGTCCT CACTGAGTTCCGCTATTGAGCGTCTGTCCTCTGGT CTGCGTATCAACAGCGCGAAAGACGATGCGGCAGG CCAGGCGATTGCTAACCGCTTCACTTCTAATATCA AAGGTCTGACTCAGGCTTCCCGTAACGCTAACGAC GGCATTTCTATTGCGCAGACCACTGAAGGTGCGCT GAATGAAATCAACAACAACCTGCAGCGTGTGCGTG AGTTGTCTGTTCAGGCCACTAACGGGACTAACTCT GATTCCGATCTGAAATCTATCCAGGATGAAATTCA GCAACGTCTGGAAGAAATCGATCGCGTTTCTAATC AGACTCAATTTAACGGTGTTAAAGTCCTGTCTCAG | |

TABLE 1-continued

| SEQ ID NO | Name | Sequence (5' -> 3') | Note |
|---|---|---|---|
| | | GACAACCAGATGAAAATCCAGGTTGGTGCTAACGA<br>TGGTGAAACCATTACCATCGATCTGCAAAAAATTG<br>ATGTGAAAAGCCTTGGCCTTGATGGGTTCAATGTT<br>AATGGGCCAAAAGAAGCGACAGTGGGTGATCTGAA<br>ATCCAGCTTCAAGAATGTTACGGGTTACGACACCT<br>ATGCAGCGGGTGCCGATAAATATCGTGTAGATATT<br>AATTCCGGTGCTGTAGTGACTGATGCAGCAGCACC<br>GGATAAAGTATATGTAAATGCAGCAAACGGTCAGT<br>TAACAACTGACGATGCGGAAAATAACACTGCGGTT<br>GATCTCTTTAAGACCACTAAATCTACTGCTGGTAC<br>CGCTGAAGCCAAAGCGATAGCTGGTGCCATTAAAG<br>GTGGTAAGGAAGGAGATACCTTTGATTATAAAGGC<br>GTGACTTTTACTATTGATACAAAAACTGGTGATGA<br>CGGTAATGGTAAGGTTTCTACTACCATCAATGGTG<br>AAAAAGTTACGTTAACTGTCGCTGATATTGCCACT<br>GGCGCGACGGATGTTAATGCTGCTACCTTACAATC<br>AAGCAAAAATGTTTATACATCTGTAGTGAACGGTC<br>AGTTTACTTTTGATGATAAAACCAAAAACGAGAGT<br>GCGAAACTTTCTGATTTGGAAGCAAACAATGCTGT<br>TAAGGGCGAAAGTAAAATTACAGTAAATGGGGCTG<br>AATATACTGCTAACGCCACGGGTGATAAGATCACC<br>TTAGCTGGCAAAACCATGTTTATTGATAAAACAGC<br>TTCTGGCGTAAGTACATTAATCAATGAAGACGCTG<br>CCGCAGCCAAGAAAAGTACCGCTAACCCACTGGCT<br>TCAATTGATTCTGCATTGTCAAAAGTGGACGCAGT<br>TCGTTCTTCTCTGGGGGCAATTCAAAACCGTTTTG<br>ATTCAGCCATTACCAACCTTGGCAATACGGTAACC<br>AATCTGAACTCCGCGCGTAGCCGTATCGAAGATGC<br>TGACTATGCAACGGAAGTTTCTAATATGTCTAAAG<br>CGCAGATTCTGCAGCAGGCTGGTACTTCCGTTCTG<br>GCGCAGGCTAACGACTACAAAGACCATGACGGTGA<br>TTATAAAGATCATGACATCGATTACAAGGATGACG<br>ATGACAAGTAG | |
| 2 | fliC_AA | MAQVINTNSLSLLTQNNLNKSQSSLSSAIERLSSG<br>LRINSAKDDAAGQAIANRFTSNIKGLTQASRNAND<br>GISIAQTTEGALNEINNNLQRVRELSVQATNGTNS<br>DSDLKSIQDEIQQRLEEIDRVSNQTQENGVKVLSQ<br>DNQMKIQVGANDGETITIDLQKIDVKSLGLDGENV<br>NGPKEATVGDLKSSFKNVTGYDTYAAGADKYRVDI<br>NSGAVVTDAAAPDKVYVNAANGQLTTDDAENNTAV<br>DLFKTTKSTAGTAEAKAIAGAIKGGKEGDTEDYKG<br>VTFTIDTKTGDDGNGKVSTTINGEKVTLTVADIAT<br>GATDVNAATLQSSKNVYTSVVNGQFTEDDKTKNES<br>AKLSDLEANNAVKGESKITVNGAEYTANATGDKIT<br>LAGKTMFIDKTASGVSTLINEDAAAAKKSTANPLA<br>SIDSALSKVDAVRSSLGAIQNREDSAITNLGNTVT<br>NLNSARSRIEDADYATEVSNMSKAQILQQAGTSVL<br>AQANDYKDHDGDYKDHDIDYKDDDDK | |

For the evaluation of the TLR5 activation ability of sgFliC secreted from SG4052, QUANTI-Blue SEAP assay was performed using HEK293/mTLR5 cell line, which is a cell line selectively and strongly expressing mouse TLR5. After SG4051 and SG4052 were grown over night (O/N), respective bacterial culture media were separated and then concentrated using a Centricon concentrator. Flagellin from the *Salmonella typhimurium* (FLA-ST) was used as a positive control for testing TLR5 activation ability.

As can be seen in FIG. 6, TLR5 was activated by the treatment with FLA-ST and SG4052 cultured media, and the activity was not observed in the SG4051 cultured media-treated group. Particularly, the treatment with SG4052 cultured media showed relatively high TLR5 stimulation compared with the treatment with FLA-ST at the same concentrations. These results indicate that FliC expressed through psgFliC possessed an equivalent degree of TLR5 activation ability to FliC of *Salmonella typhimurium*. In addition, the treatment with the extracellular matrix of attenuated *Salmonella gallinarum* containing FliC could double the TLR5-stimulating ability compared with the treatment with FliC alone.

To evaluate the tumor therapeutic ability according to the SG4052 treatment, colon tumor-forming mice were created using CT26, a cell line derived from mouse colon cancer. The CT26 bearing mice were administered SG4052 ($1\times10^8$ cfu/mice, intravenous route) at a single dose, and the tumor size was measured at 2-day intervals. PBS- and SG4051-treated groups were used as control groups in this experiment, and the tumor size was measured at 2-day intervals in the same manner (see FIG. 7). In addition, the survival rate in each group was verified by observing the survival of each group for up to 60 days (see FIG. 8). As a result of the experiment, as can be seen in FIG. 7, the tumor size decreased by a mean of 38% in the SG4051-treated group compared with the PBS-treated group, and the tumor size decreased by a mean of 76% in the SG4052-treated group compared with the PBS-treated group (18 days after bacterial infection). As can be seen in FIG. 8, regarding the survival rate of each group, the SG4051-treated group showed a survival extension of up to 10 days compared with the PBS-treated group, and the SG4052-treated group showed a survival extension of up to 32 days compared with the PBS-treated group. Particularly, the tumor completely disappeared in one animal of the SG4052-treated group. These results indicate that sgFliC-expressed attenuated *Salmonella gallinarum* has enhanced therapeutic ability compared with simple attenuated *Salmonella gallinarum.*

Example 4: Identification of M1 Macrophage Activation Ability of sgFliC-Secreted Attenuated *Salmonella gallinarum*

It was evaluated whether or not therapeutic efficacy of SG4052 induced an increase or decrease in the distribution of M1 macrophages. CT26 tumor bearing mice were administered PBS, SG4051, and SG4052, and tumor tissues were excised 8 days after inoculation. From single cells isolated from the tumor, only immune cells were primarily separated through CD45 magnetic beads. Thereafter, the cells were stained with an antibody recognizing a macrophage-specific marker, and then the macrophage distribution was measured through FACs analysis (see FIG. 9).

As a result of the experiment, as shown in FIG. 9, the distribution of M1 macrophages (MHC $II^+$, CD206−) increased by a mean of 0.7 times in the SG4051-treated group compared with the PBS-treated group, and the distribution of M1 macrophages increased by a mean of 4.5 times in the SG4052-treated group compared with the PBS-treated group. The distribution of M2 macrophages (MHC $II^+$, $CD206^+$) having immunosuppressive activity decreased by a mean of 3 times in both the SG4051-treated group and the SG4052-treated group compared with the PBS-treated group. However, the activities of $CD4^+$ and $CD8^+$ T cells were not changed. These results validate that the mechanism of enhanced tumor therapeutic efficacy of SG4052 was attributed to an increased distribution of M1 macrophages possessing immune activation activity.

Example 5: Development of sgFliC-hIL2 and Evaluation of Efficacy Thereof

Human IL-2 (hIL2) with $CD8^+$ T cell activation ability was conjugated to FliC with extracellular secretion ability to produce attenuated *Salmonella gallinarum* producing and secreting a novel protein capable of extracellular secretion along with both TLR5 and $CD8^+$ T cell stimulating origins.

First of all, it was investigated through a structure prediction program (Alpafold program, version II) whether the conjugation of hIL2 to an end of sgFliC affected each other's structure (see FIG. 10). As a result of the investigation, the fusion protein (chimeric protein) of sgFliC (Green) and hIL2 (Red) did not affect each other's structure. The wild-type hIL2 gene sequence was conjugated to an end of the sgFliC gene sequence to prepare a construct producing a novel protein with linked sgFliC and wild-type hIL2 (psgFliC-hIL2). The prepared psgFliC-hIL2 was transformed into SG4048 to produce attenuated *Salmonella gallinarum* (SG4053) producing and secreting sgFliC-hIL2 having the sequences shown in Table 2 below. In addition, the SG4053 strain was deposited on 4 Jan. 2023 with the Korean collection for type cultures (KCTC) at Korea Research Institute of Bioscience and Biotechnology and assigned accession number KACC 15270BP.

TABLE 2

| SEQ ID NO | Name | Sequence (5' -> 3') | Note |
|---|---|---|---|
| 3 | fliC_ | ATGGCACAAGTCATTAATACAAACAGCCTGTCGCT | |
| | IL2 | GTTGACCCAGAATAACCTGAACAAATCTCAGTCCT | |
| | | CACTGAGTTCCGCTATTGAGCGTCTGTCCTCTGGT | |
| | | CTGCGTATCAACAGCGCGAAAGACGATGCGGCAGG | |
| | | CCAGGCGATTGCTAACCGCTTCACTTCTAATATCA | |
| | | AAGGTCTGACTCAGGCTTCCCGTAACGCTAACGAC | |
| | | GGCATTTCTATTGCGCAGACCACTGAAGGTGCGCT | |
| | | GAATGAAATCAACAACAACCTGCAGCGTGTGCGTG | |
| | | AGTTGTCTGTTCAGGCCACTAACGGGACTAACTCT | |
| | | GATTCCGATCTGAAATCTATCCAGGATGAAATTCA | |
| | | GCAACGTCTGGAAGAAATCGATCGCGTTTCTAATC | |
| | | AGACTCAATTTAACGGTGTTAAAGTCCTGTCTCAG | |
| | | GACAACCAGATGAAAATCCAGGTTGGTGCTAACGA | |
| | | TGGTGAAACCATTACCATCGATCTGCAAAAAATTG | |
| | | ATGTGAAAAGCCTTGGCCTTGATGGGTTCAATGTT | |
| | | AATGGGCCAAAAGAAGCGACAGTGGGTGATCTGAA | |
| | | ATCCAGCTTCAAGAATGTTACGGGTTACGACACCT | |
| | | ATGCAGCGGGTGCCGATAAATATCGTGTAGATATT | |
| | | AATTCCGGTGCTGTAGTGACTGATGCAGCAGCACC | |
| | | GGATAAAGTATATGTAAATGCAGCAAACGGTCAGT | |
| | | TAACAACTGACGATGCGGAAAATAACACTGCGGTT | |
| | | GATCTCTTTAAGACCACTAAATCTACTGCTGGTAC | |
| | | CGCTGAAGCCAAAGCGATAGCTGGTGCCATTAAAG | |
| | | GTGGTAAGGAAGGAGATACCTTTGATTATAAAGGC | |
| | | GTGACTTTTACTATTGATACAAAAACTGGTGATGA | |
| | | CGGTAATGGTAAGGTTTCTACTACCATCAATGGTG | |
| | | AAAAAGTTACGTTAACTGTCGCTGATATTGCCACT | |
| | | GGCGCGACGGATGTTAATGCTGCTACCTTACAATC | |
| | | AAGCAAAAATGTTTATACATCTGTAGTGAACGGTC | |
| | | AGTTTACTTTTGATGATAAAACCAAAAACGAGAGT | |
| | | GCGAAACTTTCTGATTTGGAAGCAAACAATGCTGT | |
| | | TAAGGGCGAAAGTAAAATTACAGTAAATGGGGCTG | |
| | | AATATACTGCTAACGCCACGGGTGATAAGATCACC | |
| | | TTAGCTGGCAAAACCATGTTTATTGATAAAACAGC | |
| | | TTCTGGCGTAAGTACATTAATCAATGAAGACGCTG | |
| | | CCGCAGCCAAGAAAAGTACCGCTAACCCACTGGCT | |
| | | TCAATTGATTCTGCATTGTCAAAAGTGGACGCAGT | |
| | | TCGTTCTTCTCTGGGGGCAATTCAAAACCGTTTTG | |
| | | ATTCAGCCATTACCAACCTTGGCAATACGGTAACC | |
| | | AATCTGAACTCCGCGCGTAGCCGTATCGAAGATGC | |
| | | TGACTATGCAACGGAAGTTTCTAATATGTCTAAAG | |
| | | CGCAGATTCTGCAGCAGGCTGGTACTTCCGTTCTG | |
| | | GCGCAGGCTAACGGTGGCGGTGGTGCTAGCGCACC | |
| | | TACTTCAAGTTCTACAAAGAAAACACAGCTACAAC | |
| | | TGGAGCATTTACTGCTGGATTTACAGATGATTTTG | |
| | | AATGGAATTAATAATTACAAGAATCCCAAACTCAC | |
| | | CAGGATGCTCACATTTAAGTTTTACATGCCCAAGA | |
| | | AGGCCACAGAACTGAAACATCTTCAGTGTCTAGAA | |
| | | GAAGAACTCAAACCTCTGGAGGAAGTGCTAAATTT | |
| | | AGCTCAAAGCAAAAACTTTCACTTAAGACCCAGGG | |
| | | ACTTAATCAGCAATATCAACGTAATAGTTCTGGAA | |
| | | CTAAAGGGATCTGAAACAACATTCATGTGTGAATA | |
| | | TGCTGATGAGACAGCAACCATTGTAGAATTTCTGA | |
| | | ACAGATGGATTACCTTTAGCCAAAGCATCATCTCA | |
| | | ACACTGACTGACTACAAAGACCATGACGGTGATTA | |
| | | TAAAGATCATGACATCGATTACAAGGATGACGATG | |
| | | ACAAGTAG | |
| 4 | fliC_ | MAQVINTNSLSLLTQNNLNKSQSSLSSAIERLSSG | |
| | IL2_ | LRINSAKDDAAGQAIANRFTSNIKGLTQASRNAND | |
| | AA | GISIAQTTEGALNEINNNLQRVRELSVQATNGTNS | |
| | | DSDLKSIQDEIQQRLEEIDRVSNQTQENGVKVLSQ | |
| | | DNOMKIQVGANDGETITIDLQKIDVKSLGLDGENV | |
| | | NGPKEATVGDLKSSFKNVTGYDTYAAGADKYRVDI | |
| | | NSGAVVTDAAAPDKVYVNAANGQLTTDDAENNTAV | |
| | | DLFKTTKSTAGTAEAKAIAGAIKGGKEGDTEDYKG | |
| | | VTFTIDTKTGDDGNGKVSTTINGEKVTLTVADIAT | |
| | | GATDVNAATLOSSKNVYTSVVNGQFTEDDKTKNES | |
| | | AKLSDLEANNAVKGESKITVNGAEYTANATGDKIT | |
| | | LAGKTMFIDKTASGVSTLINEDAAAAKKSTANPLA | |
| | | SIDSALSKVDAVRSSLGAIQNREDSAITNLGNTVT | |
| | | NLNSARSRIEDADYATEVSNMSKAQILQQAGTSVL | |
| | | AQANGGGGASAPTSSSTKKTQLQLEHLLLDLQMIL | |
| | | NGINNYKNPKLTRMLTFKFYMPKKATELKHLQCLE | |
| | | EELKPLEEVLNLAQSKNFHLRPRDLISNINVIVLE | |
| | | LKGSETTFMCEYADETATIVEFLNRWITFSQSIIS | |
| | | TLTDYKDHDGDYKDHDIDYKDDDDK | |

The expression and secretion abilities of sgFliC-hIL2 were validated by western blotting. SG4051 was used as a negative control for this experiment and SG4052 was used as a positive control for this experiment (see FIG. 11). Consequently, sgFliC-hIL2 was strongly detected in the cytoplasm and outside the cell. The expression and secretion abilities thereof were similar to those of sgFliC used as a positive control. These results indicate that sgFliC possessed a carrier ability to move a protein outside the cells in addition to characteristics as a TLR5 stimulator.

Next, respective independent functions of the sgFliC-hIL2 fusion protein were evaluated. For the test of hIL2 function, a lymphocyte cell line (HT-2) isolated from the mouse spleen was introduced. Since HT-2 is a cell line that exhibits IL-2-dependent growth, IL-2 or IL-2-containing media (ConA, Corning) needs to be used for HT-2 cell growth. The HT-2 cell line was treated with cultured media of SG4052 (SG4048 carrying psgFliC) and SG4053 (SG4048 carrying psgFliC-hIL2) at 1 μg/ml each and, after 24 hours, cell viability assay (MTT) was performed. In this experiment, the PBS-treated group was used as a negative control group and the Con A-treated group was used as a positive control group. As for cell viability, the growth of the positive control group was set as 100%, and a comparison on growth was made among the other experimental groups. Resultantly, the treatment with SG4053 cultured media (1 μg/ml) was observed to show a similar growth to the positive control group, and the growth was not observed in the negative control group and the SG4052 cultured media-treated group (see FIG. 12). These results indicate that the sgFliC-hIL2 protein possessed IL-2 function.

Next, the TLR5 activation function of sgFliC-hIL2 was investigated. In this experiment, HEK293/mTLR5 cell line, which is a cell line selectively strongly expressing mouse TLR5, was utilized while SG4051 cultured media (1 μg/ml) were used as a negative control and FLA-ST (1 ng/ml) was used as a positive control. The HEK293/mTLR5 cell line was treated with cultured media (1 μg/ml) of SG4052 and SG4053 each and, after 24 hours, QUANTI-Blue SEAP assay was performed. Consequently, the SG4053 cultured media-treated group was observed to show similar or high activity compared with the positive control group (see FIG. 13). These results indicate that sgFliC-hIL2, secreted from attenuated *Salmonella gallinarum*, possessed TLR5 activation activity.

Example 6: Evaluation of Anti-Tumor Efficacy of sgFliC-IL2-Secreted Attenuated *Salmonella gallinarum*

To evaluate the tumor therapeutic ability according to the SG4053 treatment, CT26 bearing mice was produced. In this experiment, a PBS-treated group was used as a negative control group, and a SG4051- or SG4052-treated group was used as a positive control group. Like in the example above, the tumor size was measured at 2-day intervals for 18 days (see FIG. 14), and the survival rate of each group was investigated (see FIG. 15).

As a result of the experiment, the tumor size decreased by a mean of 38% in the SG4051-treated group compared with the PBS-treated group, a mean of 69% in the SG4052-treated group compared with the PBS-treated group, and a mean of 84% in the SG4053-treated group compared with the PBS-treated group. As for the survival rate in each group, the survival extended by up to 10 days in the SG4051-treated group compared with the PBS-treated group, up to 35 days in the SG4052-treated group compared with the PBS-treated group, and up to 42 days in the SG4053-treated group compared with the PBS-treated group. Particularly, the tumor completely disappeared in one animal in the SG4052-treated group and three animals in the SG4053-treated group. These results indicate that sgFliC-hIL2 secreted from attenuated *Salmonella gallinarum* showed maximized therapeutic ability compared with existing attenuated *Salmonella gallinarum* or sgFliC-secreted attenuated *Salmonella gallinarum*.

Example 7: Evaluation of Immune Cell Activation Ability of sgFliC-IL2-Secreted Attenuated *Salmonella gallinarum*

As identified in Example 6, sgFliC-IL2 secreted from SG4053 had an enhanced therapeutic efficacy in CT26 bearing mice. Hence, it was investigated whether the mechanism of enhanced therapeutic ability of SG4053 was attributed to the activation of immune cells in tumors.

To observe a change in the immune cell distribution, CT26 bearing mice were administered PBS (100 μl/mice), SG4051 ($1\times10^8$ cfu/mice), SG4052 ($1\times10^8$ cfu/mice), and SG4053 ($1\times10^8$ cfu/mice), and 8 days after administration, single cells were isolated from tumor tissues. $CD45^+$ lymphocytes recovered through CD45 magnetic beads were stained with a specific antibody recognizing an immune cell-specific marker. Thereafter, the distribution of each type of immune cells was analyzed through FACs assay. The distribution results of the macrophage M1 ($F4/80^+$, MHC $II^+$, $CD206^-$) or M2 ($F4/80^+$, MHC $II^+$, $CD206^+$) in tumors are shown in FIG. 16. As a result of the experiment, as can be seen in FIG. 16, sgFliC secreted from SG4052 and sgFliC-IL2 secreted from SG4053 increased the distribution of M1 macrophages in tumors by a mean of 4.5 and 9.4 times compared with the negative control, respectively. SG4051 (SG4048 carrying pMock) increased the distribution of M1 macrophages by a mean of 1.7 times compared with the negative control, but there was no difference in the comparison between groups (P-value). It was also observed that the M1 macrophages increased by a mean of 2.64 times in SG4052 compared with SG4051 and a mean of 5.5 times in SG4053 compared with SG4051. M2 macrophages, which function to inhibit immune activity, commonly decreased in all the groups treated with SG4051, SG4052, and SG4053 (PBS vs SG4051: a mean decrease of 65%, PBS vs SG4052: a mean decrease of 69%, PBS vs SG4053: a mean decrease of 72%), but no differences were observed in the relative comparisons among the groups SG4051, SG4052, and SG4053. These results indicate that sgFliC or sgFliC-hIL2 secreted from attenuated *Salmonella gallinarum* selectively increases the distribution of M1 macrophages possessing immune activation ability but has no direct effect on a decrease in the M2 macrophage distribution.

Next, it was investigated whether the mechanism of enhanced therapeutic efficacy was attributed to a change in T cell distribution. The distributions of $CD4^+$ T cells ($CD3^+$, $CD4^+$), $CD8^+$ T cells ($CD3^+$, $CD8^+$) and effector $CD8^+$ T cells ($CD3^+$, $CD8^+$, $CD4^{High}$, $CD62L^{Low}$) and the $CD8^+/CD4^+$ ratio in tumors were analyzed, and the results are shown in FIG. 17. No specific increase or decrease in the distribution of $CD4^+$ T cells in tumor was not observed in the SG4051-, SG4052-, and SG4053-treated groups compared with the PBS-treated group. The distributions of $CD8^+$ T cells and effector $CD8^+$ T cells in tumors increased by the administration of SG4053. In addition, the proportion of $CD8^+$ T cells was confirmed to increase through the analysis of $CD8^+/CD4^+$ ratio in tumors. These results indicate that sgFliC-hIL2 secreted from attenuated *Salmonella gallinarum* selectively increases $CD8^+$ T cells in tumors and increased $CD8^+$ T cells shows a representative mechanism of enhanced therapeutic efficacy by the SG4053 treatment.

What is claimed is:

1. A method for treating, preventing, alleviating, or inhibiting cancer, comprising administering to a subject in need thereof a pharmaceutical composition comprising as an active ingredient, a *Salmonella gallinarum* strain into which a vector containing a polynucleotide encoding IL-2 (interleukin-2) fused with FliC (a filament structural protein) is introduced, wherein the polynucleotide encoding IL-2 fused with FliC includes the sequence of SEQ ID NO: 3.

* * * * *

SEQUENCE LISTING

```
Sequence total quantity: 4
SEQ ID NO: 1            moltype = DNA  length = 1551
FEATURE                 Location/Qualifiers
source                  1..1551
                        mol_type = other DNA
                        organism = synthetic construct
SEQUENCE: 1
atggcacaag tcattaatac aaacagcctg tcgctgttga cccagaataa cctgaacaaa  60
tctcagtcct cactgagttc cgctattgag cgtctgtcct ctggtctgcg tatcaacagc  120
gcgaaagacg atgcggcagg ccaggcgatt gctaaccgct tcacttctaa tatcaaaggt  180
ctgactcagg cttcccgtaa cgctaacgac ggcatttcta ttgcgcagac cactgaaggt  240
gcgctgaatg aaatcaacaa caacctgcag cgtgtgcgtg agttgtctgt tcaggccact  300
aacgggacta actctgattc cgatctgaaa tctatccagg atgaaattca gcaacgtctg  360
gaagaaatcg atcgcgtttc taatcagact caatttaacg gtgttaaagt cctgtctcag  420
gacaaccaga tgaaaatcca ggttggtgct aacgatggtg aaaccattac catcgatctg  480
caaaaaattg atgtgaaaag ccttggcctt gatgggttca atgttaatgg gccaaaagaa  540
gcgacagtgg gtgatctgaa atccagcttc aagaatgtta cgggttacga cacctatgca  600
gcgggtgccg ataaatatcg tgtagatatt aattccggtg ctgtagtgac tgatgcagca  660
gcaccggata aagtatatgt aaatgcagca aacggtcagt taacaactga cgatgcggaa  720
aataacactg cggttgatct ctttaagacc actaaatcta ctgctggtac cgctgaagcc  780
aaagcgatag ctggtgccat taaaggtggt aaggaaggag atacctttga ttataaaggc  840
gtgactttta ctattgatac aaaaactggt gatgacggta atggtaaggt ttctactacc  900
atcaatggtg aaaaagttac gttaactgtc gctgatattg ccactggcgc gacggatgtt  960
aatgctgcta ccttacaatc aagcaaaaat gtttatacat ctgtagtgaa cggtcagttt  1020
acttttgatg ataaaaccaa aaacgagagt gcgaaacttt ctgatttgga agcaaacaat  1080
gctgttaagg gcgaaagtaa aattacagta aatggggctg aatatactgc taacgccacg  1140
ggtgataaga tcaccttagc tggcaaaacc atgtttattg ataaaacagc ttctggcgta  1200
agtacattaa tcaatgaaga cgctgccgca gccaagaaaa gtaccgctaa cccactggct  1260
tcaattgatt ctgcattgtc aaaagtggac gcagttcgtt cttctctggg ggcaattcaa  1320
aaccgttttg attcagccat taccaacctt ggcaatacgg taaccaatct gaactccgcg  1380
cgtagccgta tcgaagatgc tgactatgca acggaagttt ctaatatgtc taaagcgcag  1440
attctgcagc aggctggtac ttccgttctg gcgcaggcta acgactacaa agaccatgac  1500
ggtgattata aagatcatga catcgattac aaggatgacg atgacaagta g           1551

SEQ ID NO: 2            moltype = AA  length = 516
FEATURE                 Location/Qualifiers
source                  1..516
                        mol_type = protein
                        organism = synthetic construct
SEQUENCE: 2
MAQVINTNSL SLLTQNNLNK SQSSLSSAIE RLSSGLRINS AKDDAAGQAI ANRFTSNIKG  60
LTQASRNAND GISIAQTTEG ALNEINNNLQ RVRELSVQAT NGTNSDSDLK SIQDEIQQRL  120
EEIDRVSNQT QFNGVKVLSQ DNQMKIQVGA NDGETITIDL QKIDVKSLGL DGFNVNGPKE  180
ATVGDLKSSF KNVTGYDTYA AGADKYRVDI NSGAVVTDAA APDKVYVNAA NGQLTTDDAE  240
NNTAVDLFKT TKSTAGTAEA KAIAGAIKGG KEGDTFDYKG VTFTIDTKTG DDGNGKVSTT  300
INGEKVTLTV ADIATGATDV NAATLQSSKN VYTSVVNGQF TFDDKTKNES AKLSDLEANN  360
AVKGESKITV NGAEYTANAT GDKITLAGKT MFIDKTASGV STLINEDAAA AKKSTANPLA  420
SIDSALSKVD AVRSSLGAIQ NRFDSAITNL GNTVTNLNSA RSRIEDADYA TEVSNMSKAQ  480
ILQQAGTSVL AQANDYKDHD GDYKDHDIDY KDDDDK                            516

SEQ ID NO: 3            moltype = DNA  length = 1968
FEATURE                 Location/Qualifiers
source                  1..1968
                        mol_type = other DNA
                        organism = Homo sapiens
```

```
SEQUENCE: 3
atggcacaag tcattaatac aaacagcctg tcgctgttga cccagaataa cctgaacaaa  60
tctcagtcct cactgagttc cgctattgag cgtctgtcct ctggtctgcg tatcaacagc  120
gcgaaagacg atgcggcagg ccaggcgatt gctaaccgct tcacttctaa tatcaaaggt  180
ctgactcagg cttcccgtaa cgctaacgac ggcatttcta ttgcgcagac cactgaaggt  240
gcgctgaatg aaatcaacaa caacctgcag cgtgtgcgtg agttgtctgt tcaggccact  300
aacgggacta actctgattc cgatctgaaa tctatccagg atgaaattca gcaacgtctg  360
gaagaaatcg atcgcgtttc taatcagact caatttaacg gtgttaaagt cctgtctcag  420
gacaaccaga tgaaaatcca ggttggtgct aacgatggtg aaaccattac catcgatctg  480
caaaaaattg atgtgaaaag ccttggcctt gatgggttca atgttaatgg gccaaaagaa  540
gcgacagtgg gtgatctgaa atccagcttc aagaatgtta cgggttacga cacctatgca  600
gcgggtgccg ataaatatcg tgtagatatt aattccggtg ctgtagtgac tgatgcagca  660
gcaccggata aagtatatgt aaatgcagca aacggtcagt taacaactga cgatgcggaa  720
aataacactg cggttgatct ctttaagacc actaaatcta ctgctggtac cgctgaagcc  780
aaagcgatag ctggtgccat taaaggtggt aaggaaggag atacctttga ttataaaggc  840
gtgactttta ctattgatac aaaaactggt gatgacggta atggtaaggt ttctactacc  900
atcaatggtg aaaaagttac gttaactgtc gctgatattg ccactggcgc gacggatgtt  960
aatgctgcta ccttacaatc aagcaaaaat gtttatacat ctgtagtgaa cggtcagttt  1020
acttttgatg ataaaaccaa aaacgagagt gcgaaacttt ctgatttgga agcaaacaat  1080
gctgttaagg gcgaaagtaa aattacagta aatggggctg aatatactgc taacgccacg  1140
ggtgataaga tcaccttagc tggcaaaacc atgtttattg ataaaacagc ttctggcgta  1200
agtacattaa tcaatgaaga cgctgccgca gccaagaaaa gtaccgctaa cccactggct  1260
tcaattgatt ctgcattgtc aaaagtggac gcagttcgtt cttctctggg ggcaattcaa  1320
aaccgttttg attcagccat taccaacctt ggcaatacgg taaccaatct gaactccgcg  1380
cgtagccgta tcgaagatgc tgactatgca acggaagttt ctaatatgtc taaagcgcag  1440
attctgcagc aggctggtac ttccgttctg gcgcaggcta acggtggcgg tggtgctagc  1500
gcacctactt caagttctac aaagaaaaca cagctacaac tggagcattt actgctggat  1560
ttacagatga ttttgaatgg aattaataat tacaagaatc ccaaactcac caggatgctc  1620
acatttaagt tttacatgcc caagaaggcc acagaactga aacatcttca gtgtctagaa  1680
gaagaactca aacctctgga ggaagtgcta aatttagctc aaagcaaaaa ctttcactta  1740
agacccaggg acttaatcag caatatcaac gtaatagttc tggaactaaa gggatctgaa  1800
acaacattca tgtgtgaata tgctgatgag acagcaacca ttgtagaatt tctgaacaga  1860
tggattacct ttagccaaag catcatctca acactgactg actacaaaga ccatgacggt  1920
gattataaag atcatgacat cgattacaag gatgacgatg acaagtag              1968

SEQ ID NO: 4           moltype = AA  length = 655
FEATURE                Location/Qualifiers
source                 1..655
                       mol_type = protein
                       organism = Homo sapiens
SEQUENCE: 4
MAQVINTNSL SLLTQNNLNK SQSSLSSAIE RLSSGLRINS AKDDAAGQAI ANRFTSNIKG  60
LTQASRNAND GISIAQTTEG ALNEINNNLQ RVRELSVQAT NGTNSDSDLK SIQDEIQQRL  120
EEIDRVSNQT QFNGVKVLSQ DNQMKIQVGA NDGETITIDL QKIDVKSLGL DGFNVNGPKE  180
ATVGDLKSSF KNVTGYDTYA AGADKYRVDI NSGAVVTDAA APDKVYVNAA NGQLTTDDAE  240
NNTAVDLFKT TKSTAGTAEA KAIAGAIKGG KEGDTFDYKG VTFTIDTKTG DDGNGKVSTT  300
INGEKVTLTV ADIATGATDV NAATLQSSKN VYTSVVNGQF TFDDKTKNES AKLSDLEANN  360
AVKGESKITV NGAEYTANAT GDKITLAGKT MFIDKTASGV STLINEDAAA AKKSTANPLA  420
SIDSALSKVD AVRSSLGAIQ NRFDSAITNL GNTVTNLNSA RSRIEDADYA TEVSNMSKAQ  480
ILQQAGTSVL AQANGGGGAS APTSSSTKKT QLQLEHLLLD LQMILNGINN YKNPKLTRML  540
TFKFYMPKKA TELKHLQCLE EELKPLEEVL NLAQSKNFHL RPRDLISNIN VIVLELKGSE  600
TTFMCEYADE TATIVEFLNR WITFSQSIIS TLTDYKDHDG DYKDHDIDYK DDDDK       655
```